US010947593B2

(12) United States Patent
Chim et al.

(10) Patent No.: US 10,947,593 B2
(45) Date of Patent: Mar. 16, 2021

(54) BIOMARKERS FOR PREMATURE BIRTH

(71) Applicant: The Chinese University of Hong Kong, Hong Kong (CN)

(72) Inventors: Stephen Siu-Chung Chim, Hong Kong (CN); Chee Yin Cheung, Hong Kong (CN); Wan Chee Cheung, Hong Kong (CN); Tak Yeung Leung, Hong Kong (CN); Wing Shan Lee, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/547,229

(22) Filed: Aug. 21, 2019

(65) Prior Publication Data
US 2019/0376140 A1    Dec. 12, 2019

Related U.S. Application Data

(62) Division of application No. 14/902,542, filed as application No. PCT/CN2014/000608 on Jun. 20, 2014, now Pat. No. 10,428,383.

(60) Provisional application No. 61/857,975, filed on Jul. 24, 2013.

(51) Int. Cl.
*C12Q 1/6883* (2018.01)
*A61K 31/713* (2006.01)

(52) U.S. Cl.
CPC .......... *C12Q 1/6883* (2013.01); *A61K 31/713* (2013.01); *C12Q 2600/136* (2013.01); *C12Q 2600/158* (2013.01); *C12Q 2600/166* (2013.01); *C12Q 2600/178* (2013.01)

(58) Field of Classification Search
CPC ............ C12Q 2600/158; C12Q 1/6883; C12Q 2600/118; C12Q 1/6851; C12Q 1/686
See application file for complete search history.

(56) References Cited

U.S. PATENT DOCUMENTS

| | | |
|---|---|---|
| 2006/0166242 A1 | 7/2006 | Pennell et al. |
| 2006/0252068 A1 | 11/2006 | Lo |
| 2007/0237770 A1 | 10/2007 | Lai et al. |
| 2012/0252068 A1 | 3/2012 | Kassis |
| 2013/0237442 A1* | 9/2013 | Barnhart ............... C12Q 1/6876 506/9 |
| 2013/0296190 A1* | 11/2013 | Dong ................... C12Q 1/6876 506/9 |
| 2016/0003837 A1 | 1/2016 | Murtha |

FOREIGN PATENT DOCUMENTS

| | | |
|---|---|---|
| CN | 102792164 A | 11/2012 |
| EP | 1914548 A1 | 4/2008 |
| RU | 2132069 C1 | 6/1999 |
| RU | 2475752 C1 | 2/2013 |
| WO | 2004/065629 A1 | 8/2004 |
| WO | 2009/134452 A2 | 11/2009 |
| WO | 2009/134452 A3 | 11/2009 |

OTHER PUBLICATIONS

Chim, et al. "Systematic identification of spontaneous preterm birth-associated RNA transcripts in maternal plasma." PLoS One 7, No. 4 (2012).
Menon, "Spontaneous preterm birth, a clinical dilemma: etiologic, pathophysiologic and genetic heterogeneities and racial disparity." Acta obstetricia et gynecologica Scandinavica 87, No. 6 (2008): 590-600.
Enquobahrie, et al. "Early pregnancy peripheral blood gene expression and risk of preterm delivery: a nested case control study." BMC pregnancy and childbirth 9, No. 1 (2009): 56.
Iams, et al. "Primary, secondary, and tertiary interventions to reduce the morbidity and mortality of preterm birth." The lancet 371, No. 9607 (2008): 164-175.
NCBI Blast: Nucleotide sequence, blastn suite-2sequences, Query ID:105603, Query results using "Subject ID: NM_032047.5" and SEQ ID No. 3 of the instant application. Accessed and searched at blast.ncbi.nlm.nigh.gove on Mar. 13, 2019 (Year: 2019).
NCBI Blast: Nucleotide sequence, blastn suite-2sequences, Query ID:60021, Query results using "Subject ID: NM_032047.5" and SEQ ID No. 2 of the instant application. Accessed and searched at blast.ncbi.nlm.nigh.gove on Mar. 14, 2019 (Year: 2019).
NCBI Blast: Nucleotide sequence, blastn suite-2sequences, Query ID:145791, Query results using "Subject ID: NM_032047.5" and SEQ ID No. 1 of the instant application. Accessed and searched at blast.ncbi.nlm.nigh.gove on Mar. 14, 2019 (Year: 2019).
Paiva,et al. "Measurement of mRNA transcripts of very high placental expression in maternal blood as biomarkers of preeclampsia." The Journal of Clinical Endocrinology & Metabolism 96, No. 11 (2011): E1807-E1815.
Parks, et al. "Blastocyst gene expression correlates with implantation potential." Fertility and sterility 95, No. 4 (2011): 1367-1372.
Primer-BLAST search results, Input PCR template XM_005247824.3, pp. 1-23. Access and retrieved from www.ncbi.nlm.nih.gov on Jul. 25, 2017.
Primer-BLAST search results, Input PCR template XM_005247824.3, pp. 1-24. Access and retrieved from www.ncbi.nlm.nih.gov on Apr. 21, 2018.
Taniguchi et al., "Significance of human neutrophil antigben-2a (NBI) expression and neutrophil number in pregnancy", Transfusion, 44: 581-585 (Apr. 30, 2004).
Thangaratinam et al., "Association Between Thyroid Autoantibodies and Miscarriage and Preterm Birth: Meta-Analysis of Evidence," BMJ 2011;342:d2616.

\* cited by examiner

*Primary Examiner* — Dana H Shin
(74) *Attorney, Agent, or Firm* — Kilpatrick Townsend & Stockton LLP

(57) ABSTRACT

The present invention provides a method for determining increased risk of premature birth in a pregnant woman by detecting altered expression level of one or more marker genes in the woman's blood. A kit and device useful for such a method are also provided. In addition, the present invention provides a method for preventing or reducing the likelihood of premature birth.

16 Claims, 10 Drawing Sheets

Specification includes a Sequence Listing.

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: synthetic primer sequence - forward

<400> SEQUENCE: 1
ttgggcttgc tttgtttcct                    20

<210> SEQ ID NO 2

```
<211> LENGTH: 20
<212> TYPE: DNA
<213> ORGANISM: Artificial Sequence
<220> FEATURE:
<223> OTHER INFORMATION: synthetic primer sequence - reverse

<400> SEQUENCE: 2
gcctgccgat ctggtagaag                                              20

<210> SEQ ID NO 3
<211> LENGTH: 13
<212> TYPE: DNA
<213> ORGANISM: Artificial Sequence
<220> FEATURE:
<223> OTHER INFORMATION: synthetic probe sequence
<220> FEATURE:
<221> NAME/KEY: misc_feature
<222> LOCATION: (1)..(1)
<223> OTHER INFORMATION: 5' end labeled with 6-FAM
      (6-carboxyfluorescein)
<220> FEATURE:
<221> NAME/KEY: misc_feature
<222> LOCATION: (13)..(13)
<223> OTHER INFORMATION: 3' end labeled with MGB (minor groove-binding
      nonfluorescent quencher)

<400> SEQUENCE: 3
aggcccagca ttt                                                     13

<210> SEQ ID NO 4
<211> LENGTH: 25
<212> TYPE: DNA
<213> ORGANISM: Artificial Sequence
<220> FEATURE:
<223> OTHER INFORMATION: synthetic primer sequence - forward

<400> SEQUENCE: 4
gctgcctctt tgtctactgg ttcta                                        25

<210> SEQ ID NO 5
<211> LENGTH: 25
<212> TYPE: DNA
<213> ORGANISM: Artificial Sequence
<220> FEATURE:
<223> OTHER INFORMATION: synthetic primer sequence - reverse

<400> SEQUENCE: 5
gcagatatgg ttcattcaag aaaca                                        25

<210> SEQ ID NO 6
<211> LENGTH: 18
<212> TYPE: DNA
<213> ORGANISM: Artificial Sequence
<220> FEATURE:
<223> OTHER INFORMATION: synthetic probe sequence
<220> FEATURE:
<221> NAME/KEY: misc_feature
<222> LOCATION: (1)..(1)
<223> OTHER INFORMATION: 5' end labeled with 6-FAM
      (6-carboxyfluorescein)
<220> FEATURE:
<221> NAME/KEY: misc_feature
<222> LOCATION: (18)..(18)
<223> OTHER INFORMATION: 3' end labeled with MGB (minor groove-binding
      nonfluorescent quencher)

<400> SEQUENCE: 6
aatcaaaggg cgaccact                                                18
```

```
<210> SEQ ID NO 7
<211> LENGTH: 23
<212> TYPE: DNA
<213> ORGANISM: Artificial Sequence
<220> FEATURE:
<223> OTHER INFORMATION: synthetic primer sequence - forward

<400> SEQUENCE: 7
ggcctcgtct agagagccta gtg                                              23

<210> SEQ ID NO 8
<211> LENGTH: 18
<212> TYPE: DNA
<213> ORGANISM: Artificial Sequence
<220> FEATURE:
<223> OTHER INFORMATION: synthetic primer sequence - reverse

<400> SEQUENCE: 8
tgcgttctcc atgcaggg                                                    18

<210> SEQ ID NO 9
<211> LENGTH: 22
<212> TYPE: DNA
<213> ORGANISM: Artificial Sequence
<220> FEATURE:
<223> OTHER INFORMATION: synthetic probe sequence
<220> FEATURE:
<221> NAME/KEY: misc_feature
<222> LOCATION: (1)..(1)
<223> OTHER INFORMATION: 5' end labeled with 6-FAM
      (6-carboxyfluorescein)
<220> FEATURE:
<221> NAME/KEY: misc_feature
<222> LOCATION: (22)..(22)
<223> OTHER INFORMATION: 3' end labeled with MGB (minor groove-binding
      nonfluorescent quencher)

<400> SEQUENCE: 9
tgacctatat caatgctatc ag                                               22

<210> SEQ ID NO 10
<211> LENGTH: 20
<212> TYPE: DNA
<213> ORGANISM: Artificial Sequence
<220> FEATURE:
<223> OTHER INFORMATION: synthetic primer sequence - forward

<400> SEQUENCE: 10
acccggtgca gctagaagtc                                                  20

<210> SEQ ID NO 11
<211> LENGTH: 24
<212> TYPE: DNA
<213> ORGANISM: Artificial Sequence
<220> FEATURE:
<223> OTHER INFORMATION: synthetic primer sequence - reverse

<400> SEQUENCE: 11
gaatagggtc ttcctccttg aaca                                             24

<210> SEQ ID NO 12
<211> LENGTH: 15
<212> TYPE: DNA
<213> ORGANISM: Artificial Sequence
<220> FEATURE:
<223> OTHER INFORMATION: synthetic probe sequence
<220> FEATURE:
<221> NAME/KEY: misc_feature
<222> LOCATION: (1)..(1)
```

```
<223> OTHER INFORMATION: 5' end labeled with 6-FAM
      (6-carboxyfluorescein)
<220> FEATURE:
<221> NAME/KEY: misc_feature
<222> LOCATION: (15)..(5)
<223> OTHER INFORMATION: 3' end labeled with MGB (minor groove-binding
      nonfluorescent quencher)

<400> SEQUENCE: 12
ttgctccagg cccct                                                    15

<210> SEQ ID NO 13
<211> LENGTH: 19
<212> TYPE: DNA
<213> ORGANISM: Artificial Sequence
<220> FEATURE:
<223> OTHER INFORMATION: synthetic primer sequence - forward

<400> SEQUENCE: 13
ttcagcctcc ccaccttct                                                19

<210> SEQ ID NO 14
<211> LENGTH: 21
<212> TYPE: DNA
<213> ORGANISM: Artificial Sequence
<220> FEATURE:
<223> OTHER INFORMATION: synthetic primer sequence - reverse

<400> SEQUENCE: 14
ggtgtggaag tcagccaact g                                             21

<210> SEQ ID NO 15
<211> LENGTH: 14
<212> TYPE: DNA
<213> ORGANISM: Artificial Sequence
<220> FEATURE:
<223> OTHER INFORMATION: synthetic probe sequence
<220> FEATURE:
<221> NAME/KEY: misc_feature
<222> LOCATION: (1)..(1)
<223> OTHER INFORMATION: 5' end labeled with 6-FAM
      (6-carboxyfluorescein)
<220> FEATURE:
<221> NAME/KEY: misc_feature
<222> LOCATION: (14)..(14)
<223> OTHER INFORMATION: 3' end labeled with MGB (minor groove-binding
      nonfluorescent quencher)

<400> SEQUENCE: 15
cagccacctc tctt                                                     14
```

BIOMARKERS FOR PREMATURE BIRTH

RELATED APPLICATIONS

This application is a divisional application of U.S. application Ser. No. 14/902,542, filed Dec. 31, 2015, which is a 371 of PCT/CN2014/000608, International Filing Date Jun. 20, 2014, which claims priority to U.S. Provisional Patent Application No. 61/857,975, filed Jul. 24, 2013, the contents of which are incorporated by reference in the entirety.

BACKGROUND OF THE INVENTION

In humans, premature birth or preterm birth refers to birth at a gestational age of less than 37 weeks. Premature birth is one of the leading causes of infant deaths worldwide. Infants born prematurely are also more likely to suffer from various complications both in short term and in long term, including disabilities and impediments in growth and mental development. While substantial progress has been made to improve the survival rate and subsequent development of infants who were born prematurely, the precise cause of premature birth is yet to be fully understood. Given the prevalence and implications of premature birth, there exists a need for new methods to more accurately detect an increased risk of premature birth in pregnant women, such that preventive measures may be timely taken to reduce or eliminate the chances of premature birth. This invention fulfills this and other related needs.

BRIEF SUMMARY OF THE INVENTION

The present inventors discovered that the transcription of certain marker genes, as seen at the mRNA level, in a pregnant woman's blood cells may be elevated or suppressed in correlation with the likelihood of premature birth. As such, in a first aspect, the present invention provides a method for determining the risk a pregnant woman's risk of delivering the infant prematurely. The method includes the steps of: (a) measuring mRNA level of a marker, which may be one of the genes listed in Table 2 or CD16A or CD62L, in a blood sample taken from a pregnant woman; and (b) comparing the mRNA level obtained in step (a) with a standard control. When an increase or decrease in the mRNA level when compared with the standard control is detected, it indicates the woman having increased risk of premature birth. For any particular marker whether an increase or decrease indicates the increased risk will be apparent based on the information provide in this application, e.g., Table 2. For example, when the marker is B3GNT5, CD16A, or CD62L, an increase in the mRNA level when compared with the standard control indicates the woman having increased risk of premature birth, whereas when the marker is CLC or GBP3, a decrease in the mRNA level when compared with the standard control indicates the woman having increased risk of premature birth. Whole blood and various blood fractions such as serum or plasma or isolated blood cells can be used in this method.

In some embodiments, the mRNA level is normalized over the mRNA level of a reference gene in the same sample prior to step (b). For example, the mRNA level of a marker gene may be expressed as a ratio over the mRNA level of a reference gene. An exemplary reference gene is GAPDH. In some cases, the mRNA level of more than one marker genes is measured and compared with their respective standard controls to determine the risk of premature birth.

In some embodiments, step (a) comprises mass spectrometry or hybridization to a microarray, fluorescence probe, or molecular beacon. In some embodiments, step (a) comprises an amplification reaction, such as a polymerase chain reaction (PCR), especially a reverse transcriptase-polymerase chain reaction (RT-PCR) including quantitative RT-PCT (qRT-PCR). In some embodiments, step (a) comprises a polynucleotide hybridization assay utilizing a polynucleotide probe comprising a detectable moiety. For example, the polynucleotide hybridization assay may be a Southern Blot analysis, Northern Blot analysis, or an in situ hybridization assay.

In certain embodiments, when a pregnant woman has been indicated as having increased risk of premature delivery, the method may further include a therapeutic step to reduce or eliminate the risk of premature birth.

In a second aspect, the present invention provides a kit for determining risk of premature birth in a pregnant woman. The kit includes these components: (1) a standard control that provides an average level of a marker gene mRNA; and (2) an agent that specifically and quantitatively identifies the marker gene mRNA. The marker gene is selected from the group consisting of the genes in Table 2, CD16A, and CD62L. In some embodiments, the agent is a polynucleotide probe that hybridizes with the marker gene mRNA. The polynucleotide probe optionally includes a detectable moiety. In some embodiments, the kit further includes two oligonucleotide primers for specifically amplifying, in an amplification reaction, at least a segment of the marker gene cDNA or at least a segment of the complement of the marker gene cDNA. Often the kit further contains an instruction manual.

In a third aspect, the present invention provides a method for reducing the risk of premature birth or preventing premature birth. The method includes the step of administering to the woman an effective amount of (1) an antisense polynucleotide sequence or an siRNA against a marker gene in Table 2, or against CD16A or CD62L; or (2) an expression cassette comprising the cDNA sequence of a marker gene in Table 2 and directing the transcription of the marker gene. In some embodiments, the expression cassette comprises a promoter operably linked to the marker cDNA sequence. The selection of (1) or (2) is based on whether a particular marker RNA is found to be elevated in associate with premature birth.

The whiskers are drawn down to the 10th percentile and up to the 90th. Points below and above the whiskers are drawn as individual dots.

Figure 4:
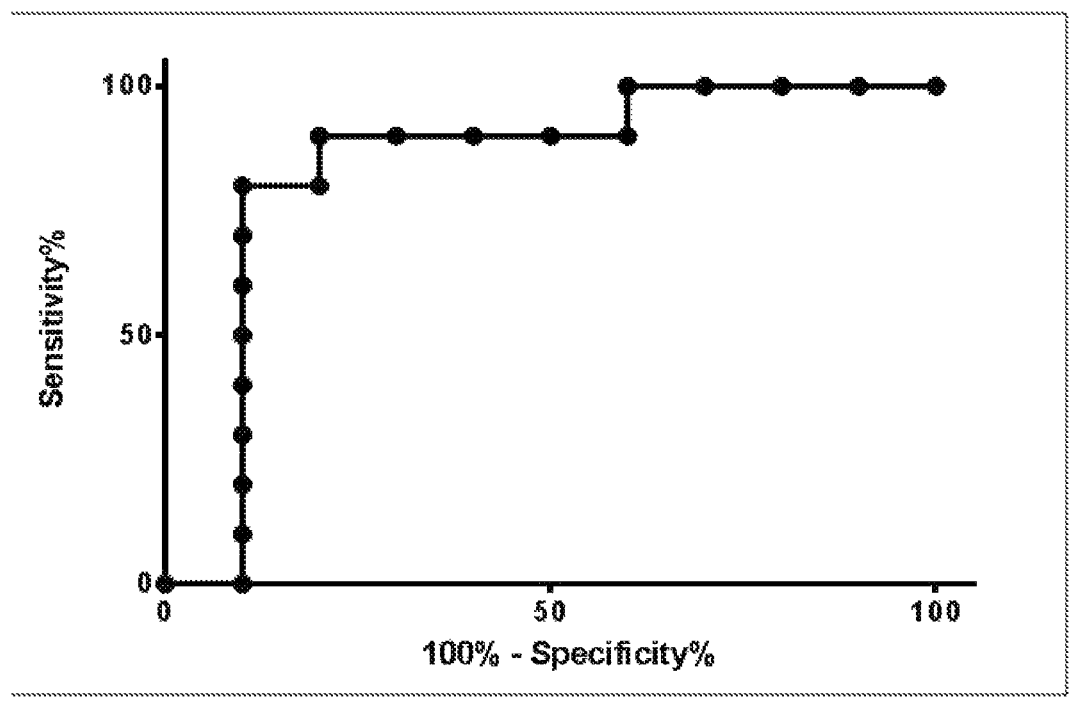

FIG. 4: Receiver-operating characteristics curve of the CLC mRNA for predicting birth sooner than 34 gestational weeks among symptomatic women.

Figure 5:
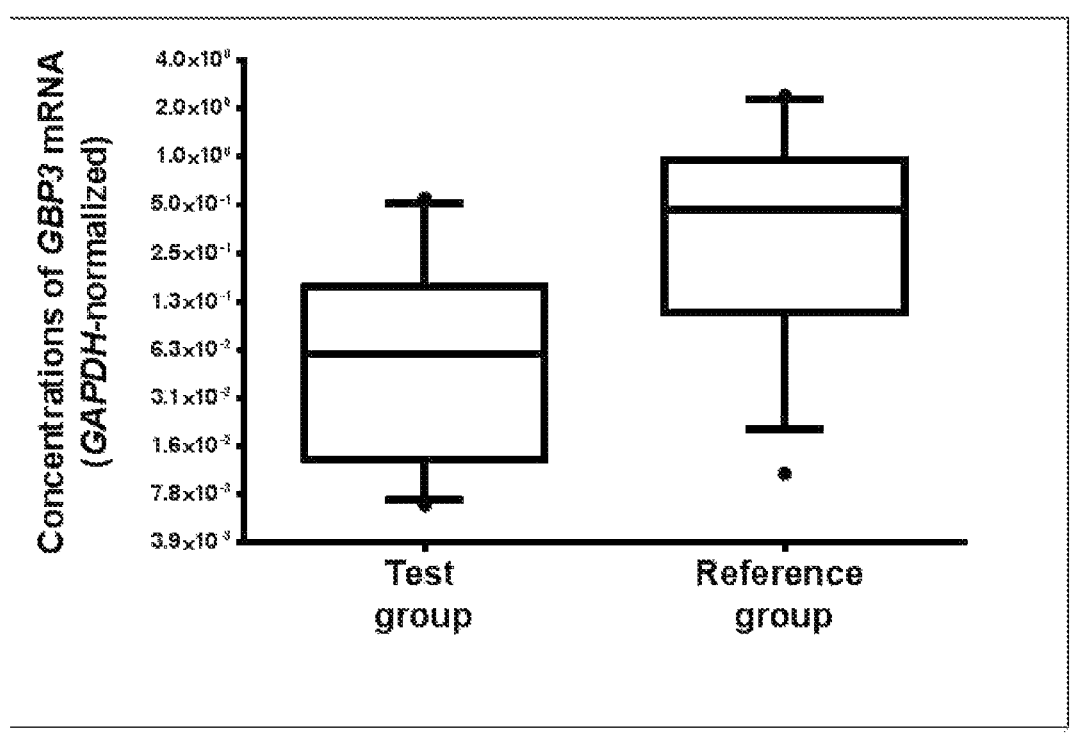

FIG. 5: Box plots of concentrations of the GBP3 mRNA in blood of symptomatic women resulting in birth sooner than 34 gestational weeks (test group) and those resulting in birth on or later than 37 weeks (reference group). The box is drawn down to the 25th percentile and up to the 75th percentile. The line inside the box is drawn as the median. The whiskers are drawn down to the 10th percentile and up to the 90th. Points below and above the whiskers are drawn as individual dots.

Figure 6:
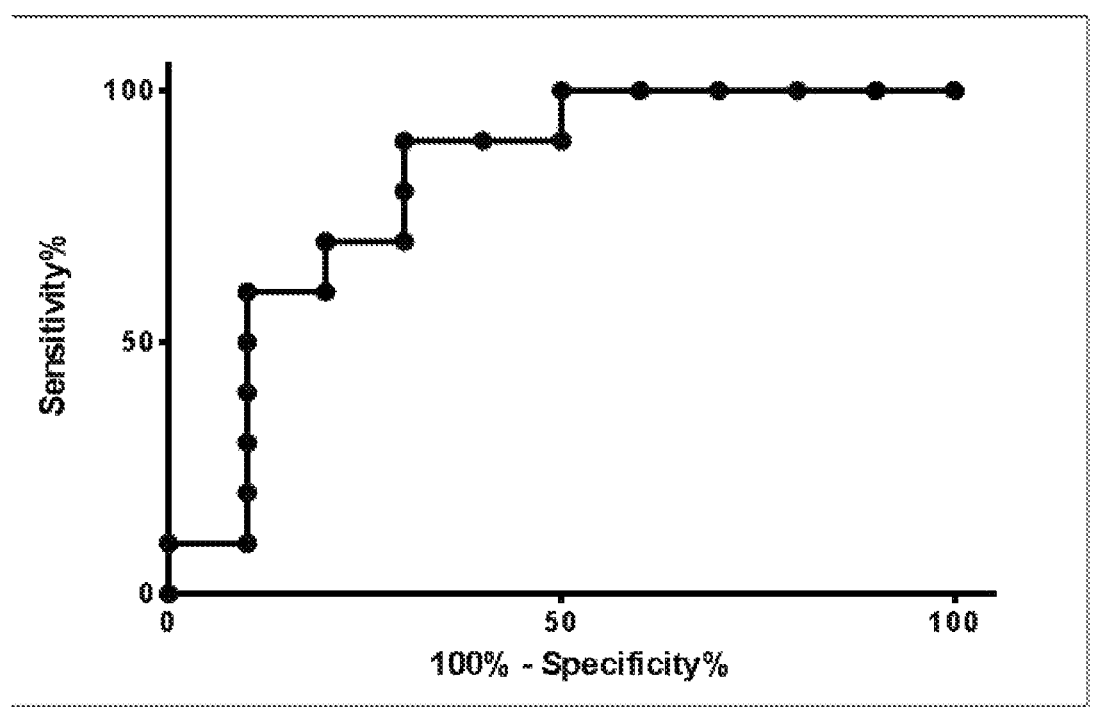

FIG. 6: Receiver-operating characteristics curve of the GBP3 mRNA for predicting birth sooner than 34 gestational weeks among symptomatic women.

Figure 7:
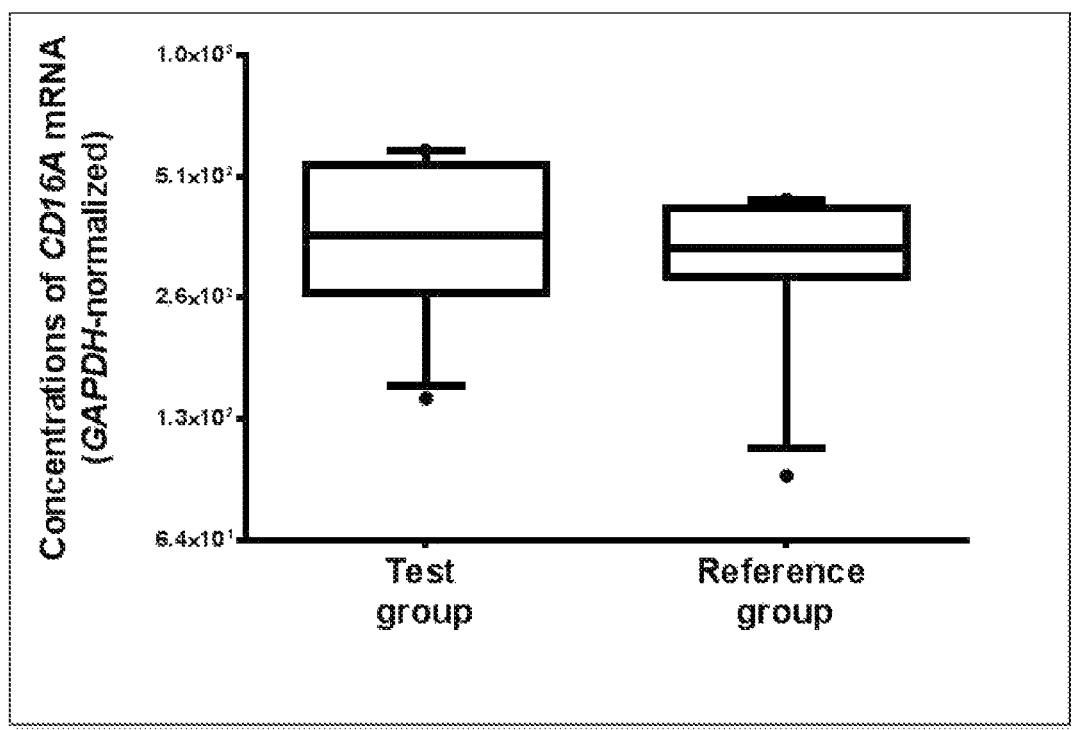

FIG. 7: Box plots of concentrations of the CD16A mRNA in blood of symptomatic women resulting in birth sooner than 34 gestational weeks (test group) and those resulting in birth on or later than 37 weeks (reference group). The box is drawn down to the 25th percentile and up to the 75th percentile. The line inside the box is drawn as the median. The whiskers are drawn down to the 10th percentile and up to the 90th. Points below and above the whiskers are drawn as individual dots.

Figure 8:
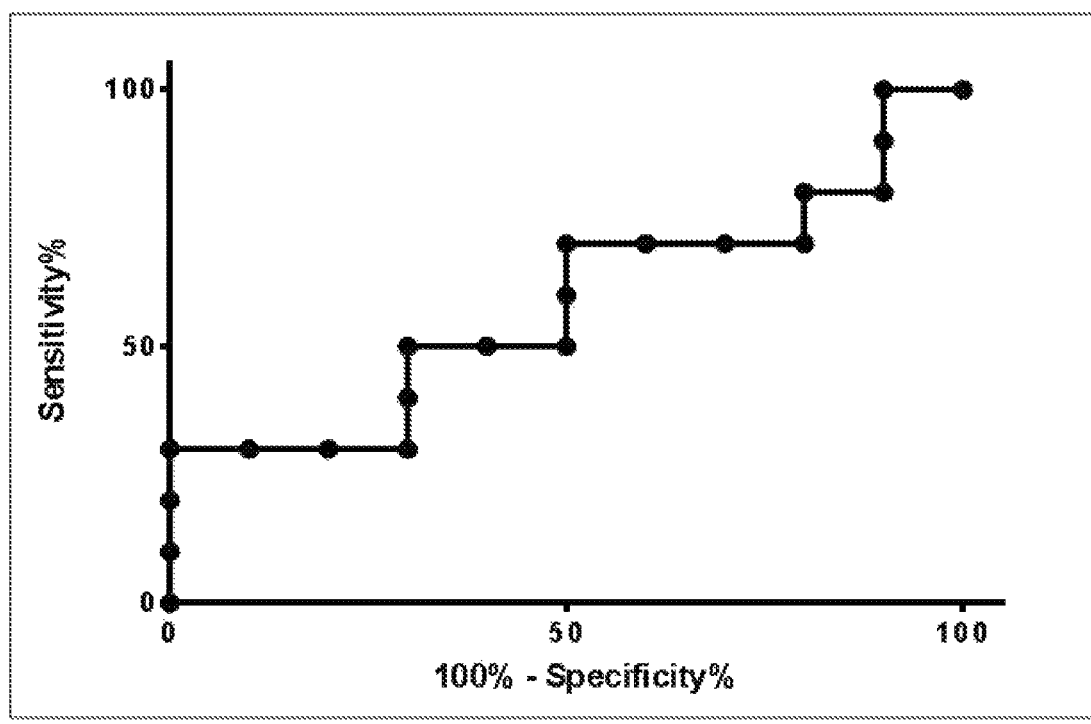

FIG. 8: Receiver-operating characteristics curve of the CD16A mRNA for predicting birth sooner than 34 gestational weeks among symptomatic women.

Figure 9:
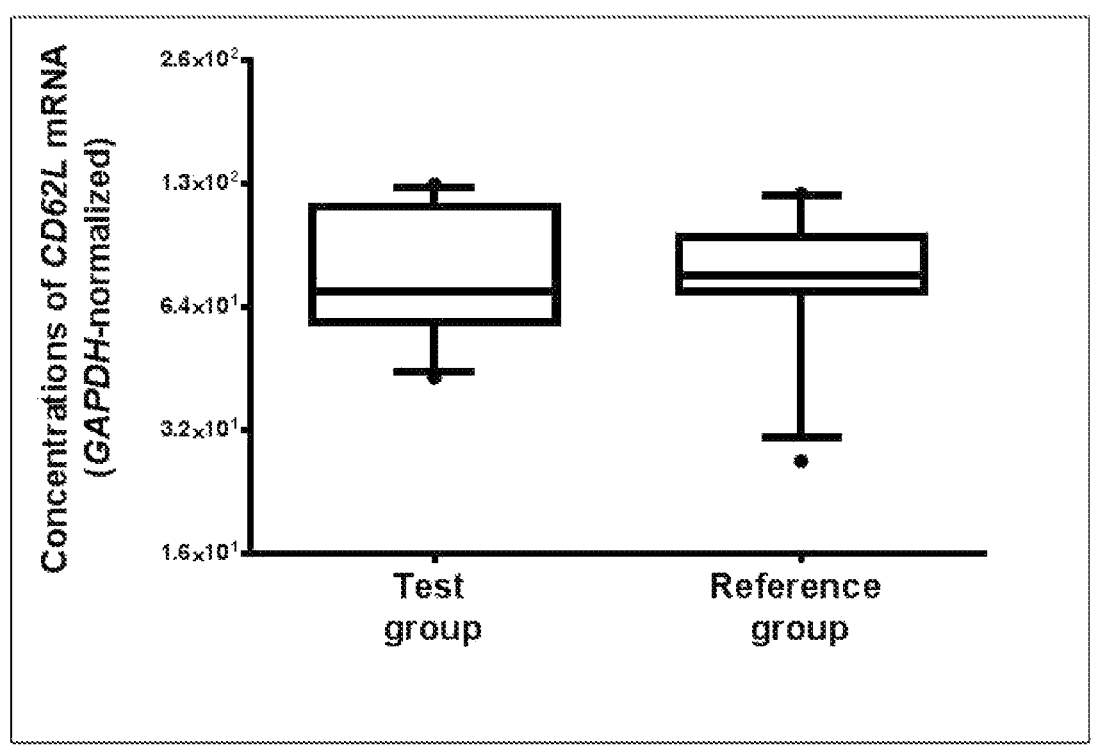

FIG. 9: Box plots of concentrations of the CD62L mRNA in blood of symptomatic women resulting in birth sooner than 34 gestational weeks (test group) and those resulting in birth on or later than 37 weeks (reference group). The box is drawn down to the 25th percentile and up to the 75th percentile. The line inside the box is drawn as the median. The whiskers are drawn down to the 10th percentile and up to the 90th. Points below and above the whiskers are drawn as individual dots FIG. 10: Receiver-operating characteristics curve of the CD62L mRNA for predicting birth sooner than 34 gestational weeks among symptomatic women.

DEFINITIONS

In this disclosure the terms "premature birth" and "preterm birth" have the same meaning and refer to the birth of a human infant at less than 37 weeks of gestational age, for example, at a gestational age of 34 weeks or less.

In this disclosure the term "or" is generally employed in its sense including "and/or" unless the content clearly dictates otherwise.

The term "blood" as used herein refers to a blood sample or preparation from a subject being tested. The term encompasses whole blood or any fractions of blood, which may contain blood cells or may be virtually acellular, such as plasma or serum.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" is used to describe the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons). As used in this application, a gene when specifically identified by its name (e.g., any one listed in Table 2 plus CD16A and CD62L) encompasses any naturally occurring variants or mutants of that gene. For example, cDNA sequence of the human B3GNT5 gene is set forth in GenBank Accession No. NM_032047. A "B3GNT5 gene" within the meaning of this application includes variants having a polynucleotide sequence with at least 80%, 85%, 90%, 95%, 98%, 99% or higher sequence identity to the cDNA sequence of NM_032047. Percentage sequence identity for other genes including those provided in Table 2 is expressed in a similar manner. The GenBank Accession No. for CD16A is NM_000569, NM_001127592, NM_001127593, NM_001127595, or NM_001127596 and for CD62L is NM_000655 or NR 029467.

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant B3GNT5 gene used in the method of this invention has at least 80% sequence identity, preferably 85%, 90%, 91%, 92%, 93, 94%, 95%, 96%, 97%, 98%, 99%, or 100% identity, to a reference sequence, e.g., a wild-type human B3GNT5 cDNA set forth in GenBank Accession No. NM_032047), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average level of a marker gene mRNA found in the blood of pregnant woman who delivers the infant in a normal time frame of her pregnancy). An increase is a positive change that is typically at least 10%, or at least 20%, or 50%, or 100%, and can be as high as at least 2-fold, 3-fold, 4-fold, 5-fold, 6-fold, 7-fold, 8-fold, 9-fold, or 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a marker gene (any one listed in Table 2 and further including CD16A and CD62L), e.g., the cDNA or genomic sequence for human B3GNT5 gene or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. In this disclosure the term "primer pair" means a pair of primers that hybridize to opposite strands a target DNA molecule or to regions of the target DNA which flank a nucleotide sequence to be amplified. In this disclosure the term "primer site" means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence, e.g., mRNA of any one of the marker genes listed in Table 2 plus CD16A and CD62L, that is present in a blood sample taken from a healthy pregnant woman or a pregnant woman with frequent uterine contractions before 37 gestational weeks, and who delivers the infant within the normal time frame of her pregnancy. The standard control value is suitable for the use of a method of the present invention, to serve as a basis for comparing the amount of a marker gene mRNA that is present in a test sample. An established sample serving as a standard control provides an average amount of a marker mRNA that is typical for a blood sample of an average, healthy pregnant woman or a pregnant woman with frequent uterine contractions before 37 gestational weeks and who delivers her infant within normal time frame of her pregnancy as conventionally defined. A standard control value may vary depending on the nature of the sample (e.g., how it has been processed after collection), whether the mRNA level is normalized over the level of mRNA of another reference gene (e.g., the ratio between the marker mRNA level and the reference mRNA), as well as other factors such as the age, gestational age, and ethnicity of the subjects based on whom such a control value is established.

The term "reference gene," as used herein refers to a "housekeeping" gene that is known to be consistently expressed at a readily detectable and substantially constant level in the blood samples. Examples of such "housekeeping" genes for blood samples include GAPDH (glyceraldehyde 3-phosphate dehydrogenase), SDHA (succinate dehydrogenase), HPRT1 (hypoxanthine phosphoribosyl transferase 1), HBS1L (HBS1-like protein), AHSP (alpha haemoglobin stabilising protein), ACTB (beta-actin), RNA18S5 (RNA, 18S ribosomal 5), FCGR3A (the Fc fragment of IgG, low affinity Ma, receptor), FCGR3B (the Fc fragment of IgG, low affinity Ma, receptor), B2M(beta-2-microglobulin), HUWE1 (HECT, UBA and WWE domain containing 1, E3 ubiquitin protein ligase), TPT1 (tumor protein, translationally-controlled 1), MYL12B (myosin, light chain 12B, regulatory), SKP1 (S-phase kinase-associated protein 1) and any genes identified as suitable for normalization of expression data from blood samples (Chang et al., 2011; Cheng et al., 2011). Multiple "housekeeping genes" may also be used.

The term "average," as used in the context of describing a pregnant woman who is healthy, or a pregnant woman with frequent uterine contractions before 37 gestational weeks, and who is later confirmed to deliver within the normal time frame of her pregnancy, refers to certain characteristics, especially the amount of certain marker gene mRNA found in the woman's blood sample that are representative of a randomly selected group of healthy pregnant women, or pregnant women with frequent uterine contractions before 37 gestational weeks, and who are later confirmed to deliver within the normal time frame of pregnancy. This selected group should comprise a sufficient number of women such that the average amount of the marker mRNA in the blood of these individuals reflects, with reasonable accuracy, the corresponding amount of the marker mRNA in the general population of healthy pregnant women, or pregnant women with frequent uterine contractions before 37 gestational weeks, and who deliver their infants in the normal time frame of pregnancy. In addition, the selected group of women generally have a similar gestational age to that of a subject whose sample is tested for the risk of premature delivery. Moreover, other factors such as age, ethnicity, medical history are also considered and preferably closely matching between the profiles of the test subject and the selected group of individuals establishing the "average" value.

The term "amount" as used in this application refers to the quantity of a polynucleotide of interest, e.g., a marker gene mRNA, present in a sample. Such quantity may be expressed in the absolute terms, i.e., the total quantity of the polynucleotide in the sample, or in the relative terms, i.e., the concentration of the polynucleotide in the sample, including expressed in the form of a ratio between the maker mRNA level and a reference mRNA level produced by a so-called normalization process.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect, for instance, to reduce the risk of the premature birth of an infant prior to 37 weeks or 34 weeks of gestational age or to prevent such premature birth.

DETAILED DESCRIPTION OF THE INVENTION

I. Introduction

Premature human birth, especially birth before 37 weeks or even before 34 weeks of gestational age, leads to increased infant mortality and developmental problems. To date, fetal fibronectin in the cervicovaginal fluids and cervical length using transvaginal ultrasonography are the clinically useful markers for predicting human birth sooner than 37 gestational weeks. For example, Lockwood et al. measured the concentrations of fetal fibronectin in cervical or vaginal fluid in 117 women with symptoms of uterine contractions and intact membrane. Using >50 ng/mL as a threshold, Lockwood et al. predicted women who delivered before 37 gestational weeks at a sensitivity of 81.7% and a specificity of 82.5% (Lockwood et al. 1991). Recently, a systematic review on multiple similar studies has estimated that this test could predict birth before 34 weeks among symptomatic women at a sensitivity of 74.6% and specificity of 79.5% (Honest et al. 2003).

On the other hand, Murakawa et al. measured the cervical length using transvaginal ultrasonography in 32 women with symptoms of uterine contractions before 37 weeks. Using <25 mm as a threshold, Murakawa et al. predicted women who delivered before 37 weeks at a sensitivity of 63.6% and a specificity of 85.7% (Murakawa et al. 1993). Recently, a systematic review on multiple similar studies has estimated that this test could predict birth before 34 weeks among symptomatic women at a sensitivity of 46.2% and specificity of 93.7% (Sotiriadis et al. 2010).

Besides fetal fibronectin and cervical length, 319 studies involving 22 tests have been systematically reviewed for their performance in predicting birth before 37 weeks, and none have exceptional accuracy (Honest et al. 2012). Hence, novel markers which could predict human birth before 37 weeks with higher sensitivity and higher specificity are much needed, so that prevention and intervention can be targeted at those who are most likely to benefit.

The present inventors discovered for the first time that mRNA of several biomarkers found in a pregnant woman's blood can serve as accurate markers to indicate the likelihood of premature birth. This discovery provides important means for determining the risk of premature birth and for prophylactic treatment of premature birth. This method for predicting premature delivery may be applied to pregnant women with or without symptoms known to be associated with premature birth, such as uterine contractions before 37 gestational weeks or prelabor rupture of membrane, including to women who have experienced no regular uterine contractions but have (1) previous history of giving birth sooner than 37 weeks in previous pregnancies; (2) a shortened cervical length, funneling or sludge in the cervix; (3) signs of infection or inflammation of the reproductive tract; (4) antepartum hemorrhage; or (5) multiple pregnancies.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, Gene *Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984).

Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human B3GNT5, CLC, CD16A, or CD62L gene, and synthetic oligonucleotides (e.g., primers) can be verified using, e.g., the chain termination method for sequencing double-stranded templates of Wallace et al., Gene 16: 21-26 (1981).

III. Acquisition of Blood Samples and Analysis of Marker mRNA

The present invention relates to measuring the amount of mRNA transcribed from at least one of marker genes found in a pregnant woman's blood, especially in a plasma or serum sample, as a means to assess the risk of woman delivering the infant prematurely. The marker genes include those identified in Table 2, as well as CD16A and CD62L. Thus, the first steps of practicing this invention are to obtain a blood sample from a pregnant woman being tested and extract mRNA from the sample.

A. Acquisition and Preparation of Blood Samples

A blood sample is obtained from a pregnant woman at a gestational age suitable for testing using a method of the present invention. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation.

The analysis of mRNA transcribed from one or more marker genes found in maternal blood according to the present invention may be performed using, e.g., whole blood or any preparation of whole blood that contains the blood cells. Preparations of blood that do not contain the blood cells, such as plasma or serum, are also useful for the purpose of practicing the present invention, due to blood cells being the predominant source of nucleic acids present in the plasma or serum (Lui et al., 2002). For preparing blood cells from a sample, the methods for removing the acellular portion, such as plasma or serum, from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be separated and then removed from the celluar fraction of whole blood through centrifugation or sedimentation by gravity alone for an appropriate period of time If centrifugation is used then it is typically, though not exclusively, conducted at an appropriate speed, e.g., 1,500-3,000×g. For preparation of plasma/serum from a blood sample, the methods are also well known among those of skill in the art. For example, a blood sample collected in EDTA-containing tubes is centrifuged at 16,000×g for 10 minutes in 4° C. to remove plasma, and re-centrifuged at 1,600×g for 10 minutes in 4° C. to remove any residual plasma. Furthermore, after the whole blood, blood cells, plasma or serum have been collected or prepared, additives may be added to preserve the RNA. These additives may include monophasic solution of phenol and guanidinium isothiocyanate, or the commercially available reagents, including Trizol (Life Technologies), Trizol LS (Life Technologies), RNA Later (Life Technologies—Ambion), RNA Later ICE (Life Technologies—Ambion) and blood collection tubes associated with the PreanAlytiX system (Qiagen/Beckton Dickson). Unless otherwise stated, these commercially available reagents for preserving and/or extracting the RNA are performed according to the manufacturers' recommendations.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR Based Quantitative Determination of mRNA Level

Once mRNA is extracted from a sample, the amount of mRNA transcribed from one or more of the marker genes identified in Table 2 may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the marker gene mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention, one of skill in the art will recognize that amplification of these mRNA species in a maternal blood sample may be accomplished by any known method, such as ligase chain reaction (LCR), transcription-mediated amplification, and self-sustained sequence replication or nucleic acid sequence-based amplification (NASBA), helicase dependent amplification (HDA), rolling circle amplification (RCA) and loop-mediated isothermal amplification (LAMP), each of which provides sufficient amplification. More recently developed branched- DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The marker gene mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to marker gene mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well-known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; *Wilkinson, In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well-known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

IV. Establishing a Standard Control

In order to establish a standard control for practicing the method of this invention, a group of "healthy" pregnant women, or pregnant women with frequent uterine contractions before 37 gestational weeks, and who are later confirmed to deliver within the normal time frame of her pregnancy as determined by conventional methods is first selected. These individuals are within the appropriate parameters, such as a particular gestational age and comparable health status. Optionally, the individuals are further grouped based on similar age or similar ethnic background.

The normal delivery time of the selected individuals will be confirmed later on, and anyone among the selected individuals who turn out to give birth sooner or later than the normal delivery time frame will be excluded from the group to provide data as a "standard control."

Furthermore, the selected group of individuals must be of a reasonable size, such that the average amount/concentration of marker mRNA in the blood sample obtained from the group can be reasonably regarded as representative of the normal or average level among the general population of healthy pregnant women, or pregnant women with frequent uterine contractions before 37 gestational weeks, and who will give birth within the normal time frame. Preferably, the selected group comprises at least 10 human subjects.

In accordance with the fundamental scientific principle of establishing a control value, the mRNA level in the control group is determined by the same method used to determining the mRNA level in the test individuals. For example, if the mRNA level of a marker gene is determined in a particular type of sample (e.g., plasma) taken from a woman being tested, the control must be also obtained from the same type of sample. If the mRNA level of a marker gene is determined after being normalized over the mRNA level of a reference gene (e.g., represented by the ratio of a marker gene mRNA to a reference gene mRNA), then the standard control must also be represented in the form of a normalized value over the same reference gene mRNA level.

Once an average value for any one given marker mRNA is established based on the individual values found in each subject of the selected control group, this average or median is considered a standard control. A standard deviation is also determined during the same process. In some cases, separate standard controls may be established for separately defined groups having distinct characteristics such as age, gender, or ethnic background.

V. Therapeutic Methods for Preventing Premature Birth

By illustrating the correlation between the mRNA level of the marker genes identified in Table 2 and the risk of premature birth, the present invention further provides a means for prophylactically treating pregnant women who are otherwise likely to experience preterm labor and deliver their infants well before they reach the full term: once an increased or decreased marker mRNA level is detected and an increased risk of premature birth is determined, the attending physician has the option to treat the woman prophylactically, for example, with antenatal corticosteroids, which has been shown to reduce neonatal morbidity and mortality from respiratory distress, intraventricular hemorrhage, necrotizing enterocolitis, and patent ductus arteriosus (Roberts and Dalziel, 2006, Cochrane Database Syst Rev(3): CD004454; Wapner et al. 2006, Am J Obstet Gynecol 195(3): 633-42). Also, tocolytic drugs may be used to prolong pregnancy in women at high risk of giving birth too early. The use of these drugs provides a 48-hour delayed delivery, which allows transfer to a specialist unit and administration of corticosteroids to reduce neonatal morbidity and mortality (Jams et al., 2008 *Lancet* 371(9607): 164-75). In addition, treatment with transdermal glyceryl trinitrate has been reported to effectively decrease neonatal morbidity (Smith et al. 2007, *Am J Obstet Gynecol* 196(1): 37 el-8). As used herein, treatment of premature birth encompasses reducing or eliminating the likelihood of a pregnant woman giving birth any time before 37 weeks of gestational age, for example, before 34 weeks of gestational age.

Another possibility to treat premature birth is by directly regulating the mRNA level of the marker gene(s) that have been shown to deviate from a standard control value. For example, when a marker gene is found to have increased from the standard control value, measures may be taken to specifically reduce the level of mRNA of this gene. Antisense polynucleotide sequences and siRNA may be administered to the pregnant woman for this purpose. On the other hand, when a marker gene is found to have decreased from the standard control value, measures may be taken to specifically increase the level of mRNA of this gene. An isolated nucleic acid, such as an expression cassette, containing the coding sequence of the marker gene and directing the transcription of the sequence may be administered to the pregnant woman for this purpose.

VI. Kits and Devices

The invention provides compositions and kits for practicing the methods described herein to assess the mRNA level of any one marker genes (such as those listed in Table 2, as well as CD16A and CD62L) for determining the risk of premature delivery in a pregnant woman.

Kits for carrying out assays for determining the marker gene mRNA level typically include at least one oligonucleotide probe useful for specific hybridization with at least one segment of the marker gene coding sequence or its complementary sequence. Optionally, this oligonucleotide probe is labeled with a detectable moiety. In some cases, the kits may include at least two oligonucleotide primers that can be used in the amplification of at least one segment of the marker gene DNA or mRNA by PCR, particularly by RT-PCR. In some cases, the kits may contain multiple sets of the above-described probe and/or primers, such that more than one marker gene mRNA maybe tested and quantitated. In some case, the kits may further contain the above-described probe and/or primers that can be used to determine the mRNA level of a reference gene.

Often, the kits also include an appropriate standard control. The standard controls indicate the average value of one or more marker gene mRNA in a particular type of blood sample. In some cases such standard control may be provided in the form of a set value. In addition, the kits of this invention may provide instruction manuals to guide users in analyzing test samples and assessing the risk of premature birth in a test subject.

In a further aspect, the present invention can also be embodied in a device or a system comprising one or more such devices, which is capable of carrying out all or some of the method steps described herein. For instance, in some cases, the device or system performs the following steps upon receiving a blood sample, e.g., a plasma sample taken from a pregnant woman being tested for the risk of premature birth, assessing the risk of premature birth: (a) determining in the sample the amount or concentration of a marker gene mRNA, which optionally may be normalized over the mRNA level of a reference gene; (b) comparing the amount or concentration with a standard control value; and (c) providing an output indicating whether increased risk of premature birth is present. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Introduction

Currently, fetal fibronectin in the cervicovaginal fluid and cervical length determined by transvaginal ultrasonography are the best available makers for predicting human birth before 37 gestational weeks. While these methods are used for their high specificity, their sensitivity is only moderate.

The present inventors have a long-standing interest in the systematic discovery of pregnancy-associated RNA, microRNAs (Tsui et al. 2004; Chim et al. 2008) and DNA methylation markers (Chim et al. 2005; Chim et al. 2008; Tsui et al. 2010) circulating in maternal peripheral blood plasma. Of clinical interest, the inventors have discovered that certain circulating RNA transcripts are detected more frequently in women presenting with uterine contractions and resulting in birth sooner than 34 gestational weeks, but not in gestational age-matched women (Chim et al. 2012). The promising data in the cell-free maternal plasma prompted the inventors to systematically investigate if other blood compartments, including blood cells, contain RNA transcripts that may predict birth sooner than 34 weeks.

To identify such markers in a systematic and whole-genome approach, the inventors have profiled the RNA levels of almost all 30,000 human genes and their variants using the exon array technology. This technology has enabled the inventors to generate the global gene expression (RNA) profile, or transcriptome, of blood at high resolution at the exon level, which is more detailed than the gene level. The inventors have systematically profiled the transcriptomes of maternal blood obtained from women during their presentation of regular uterine contractions before 34 weeks. Of these, a panel of RNA transcripts from 32 genes has been identified to be readily measurable and differentially expressed in blood of women resulting in birth sooner than 34 weeks, compared with those resulting in birth on or later than 37 weeks.

Since human birth sooner than 34 gestational weeks are more susceptible to neonatal mortality and morbidity, birth sooner than 34 weeks has been used as an outcome measure in most parts of this study. However, such experimental design and outcome measure do not preclude discovery of markers for predicting birth before 37 weeks, or within 2-7 days of presentation of uterine contractions.

Using quantitative reverse-transcriptase polymerase chain reaction (qRT-PCR), the inventors have demonstrated that the identified blood markers, when used alone, could already be used to predict birth sooner than 34 weeks at high sensitivity and high specificity.

Methods and Results

Recruitment of Participants.

Pregnant women with regular and frequent uterine contractions (>1 every 10 minutes) before 34 gestational weeks were invited to participate in this study with informed consent. Peripheral blood was obtained from each participant during preterm uterine contraction. The delivery outcome was followed up. Women who were later confirmed to result in birth sooner than 34 weeks were categorized as the test group, and those who were later confirmed to result in birth on or later than 37 weeks were categorized as the reference group. Pregnancies involving indicated preterm birth, preeclampsia, multiple pregnancies, fetal distress, growth restriction, chromosomal or structural abnormalities were excluded.

Blood Processing.

12 mL of peripheral blood was collected into EDTA-containing tubes (Beckton Dickson) from the pregnant women during presentation of preterm uterine contraction, processed within 6 hours. Briefly, the blood was centrifuged 1,600×g. Plasma was removed. The blood sample was centrifuged again at 5,000×g for further removal of plasma. 0.3 mL of harvested blood cells were mixed with 0.9 mL Trizol LS (Invirtogen, Life Technologies), and stored at −80 degrees Celsius until RNA extraction Profiling of the Blood Transcriptomes Based on Exon Array.

For each blood sample, RNA was extracted from Trizol LS-blood cells and treated with DNase I (Invitrogen, Life Technologies) to remove genomic DNA contamination. The quantity and quality of the RNA preparations from placental tissue were assessed by spectrophotometer and Bioanalyzer (Agilent). Six blood RNA samples (3 from the test group, and another 3 from the reference group, Table 1) were analyzed using Exon 1.0ST gene expression array (Affymetrix), according to manufacturers' instructions.

Preprocessing of Exon Array Data.

The probe signal data were then analyzed using the Partek Genomics Suite (version 6.5, Partek Inc.). To normalize probe signals from different blood samples, the Robust Multi Array (RMA) normalization (Irizarry et al. 2003) was performed. Each array contains over 1,400,000 sets of probes interrogating the RNA expression levels of essentially all >30,000 human genes and transcript variants. Although the majority of the probe signals were unchanged in any microarray data, their sheer number would hamper the statistical analysis, including the multiple hypotheses testing, and hence must be removed. To this end, the inventors first performed a T-test (without adjustment for multiple testing comparison) on all probes and found that only 9,264 probes were changed between the test and reference groups.

Data Mining and Systematic Identification of Markers.

To account for the difference in gestational age at blood collection, each sample in the test group with was paired up another sample in the reference group with matched gestational age (within 1 week). To identify probes that were changed between the two groups, a paired T-test was performed on the 9,264 probes. Among them, 3,778 probes were changed between the two groups (p-values, range $5.0 \times 10^{-6}$ to 0.049). To make adjustment for multiple hypothesis testing, q-values were calculated by the False Discovery Rate method (Storey 2002), and 3500 probes were selected (q-value <0.007639). Among them, the median signals of 153 probes were changed by >2.6-fold between the two groups (72 probes and 81 probes were up-regulated and down-regulated, respectively, in the test group, compared with the reference group).

To further isolate the up-regulated probes that might potentially distinguish the two groups, the inventors searched for probes of which the first quartile of the signals in the test group was >2-fold higher than the third quartile of the signals in the reference group, and selected 52 probes fulfilling this criterion. Similarly, to further isolate the down-regulated probes that might distinguish the two groups, the inventors searched for probes of which the first percentile of the signals in the reference group was >2-fold higher than the third percentile of the signals in the reference group, and selected 72 probes fulfilling this criterion. Thus, 124 probes (=52+72) were identified with potential to distinguish the two groups.

To further refine on the RNA transcripts that would be readily detectable in the blood sample, the inventors selected only the RNA transcripts represented by >1 probe with median expression signal >169 units (=$2^{7.4}$ units) in at least one group, and identified 48 probes (14 up-regulated probes and 34 down-regulated probes). These probe signals were derived from RNA transcripts from 32 genes (13 up-regulated genes and 19 down-regulated genes). It is reasoned that this panel of 32 RNA transcripts are readily detectable in blood and can be used to predict women resulting in birth sooner than 34 weeks (Table 2).

QRT-PCR Analysis of Novel Markers Identified.

To demonstrate that markers identified using the exon array technology and the above data-mining strategy (Table 2) are useful, the inventors performed qRT-PCR, the gold-standard in gene expression profiling. Twenty blood RNA samples (10 from the test groups, another 10 from the reference group, Table 3) collected from women were analyzed.

The concentrations of 3 marker RNA transcripts identified in Table 2 were determined by qRT-PCR. Namely, the concentrations of those mRNA coding for UDP-GlcNAc: betaGal beta-1,3-N-acetylglucosaminyltransferase 5 (B3GTN5), Charcot-Leyden crystal galectin (CLC), and guanylate binding protein 3 (GBP3) were measured. The former marker RNA transcript has been shown to be up-regulated in blood of women resulting in birth sooner than 34 weeks, compared to those resulting in birth on or later than 37 weeks, while the latter two markers have been shown to be down-regulated. To control for variations in RNA input into each qRT-PCR, the marker RNA concentrations were normalized against a reference RNA, the glyceraldehyde-3-phosphate dehyrdogenase (GAPDH) mRNA.

For the B3GNT5 qRT-PCR assay, the forward primer was 5'-TTG GGC TTG CTT TGT TTC CT-3' (SEQ ID NO:1), the reverse primer was 5'-GCC TGC CGA TCT GGT AGA AG-3' (SEQ ID NO:2), and the hydrolysis probe was 5'(6FAM)-AGG CCC AGC ATT T-3'(MGB) (SEQ ID NO:3), where 6FAM was the 6-carboxyfluorescein reporter dye and MGB was the minor groove-binding nonfluorescent quencher. For the CLC qRT-PCR assay, the forward primer was 5'-GCT GCC TCT TTG TCT ACT GGT TCT A-3' (SEQ ID NO:4), the reverse primer was 5'-GCA GAT ATG GTT CAT TCA AGA AAC A-3' (SEQ ID NO:5), and the hydrolysis probe was 5(6FAM)'-AAT CAA AGG GCG ACC ACT-3'(MGB) (SEQ ID NO:6). For the GBP3 qRT-PCR assay, the forward primer was 5'-GGC CTC GTC TAG AGA GCC TAG TG-3' (SEQ ID NO:7), the reverse primer was 5'-TGC GTT CTC CAT GCA GGG-3' (SEQ ID NO:8), and the hydrolysis probe was 5'(6FAM)-TGA CCT ATA TCA ATG CTA TCA G-3'(MGB) (SEQ ID NO:9). For the GAPDH qRT-PCR assay, the sequences for primers and probe was published previously (Chim et al. 2012).

To minimize the effect of any contaminating genomic DNA in the RNA preparations, the qRT-PCR assay for all mRNA targets, except for the B3GNT5 mRNA, was designed to be intron-spanning. However, due to certain constrains of the mRNA sequence, the RT-qPCR assay for B3GNT5 mRNA did not span any intron.

For all qRT-PCR assays, except the B3GNT5 assay, each qRT-PCR was set up in a reaction volume of 25 μL using components supplied in an EZ rTth RNA PCR reagent set (Life Technologies). Each reaction contained 5 μL of 5× EZ buffer, and final concentrations of 3 mM Mn(OAc)$_2$, 300 μM each of dATP, dCTP, dGTP, 600 μM dUTP, 2.5 U of rTth polymerase, 0.25 U of uracil N-glycosylase (UNG) and 5 μL of RNA extracted from a blood sample. For the B3GNT5 assay, each qRT-PCR was set up in a reaction volume of 12.5 μL containing 2.5 μL of 5× EZ buffer, and final concentrations of 3 mM Mn(OAc)$_2$, 300 μM each of dATP, dCTP, dGTP, 600 μM dUTP, 2.5 U of rTth polymerase, 0.25 U of uracil N-glycosylase (UNG) and 2.5 μL of RNA extracted from a blood sample. For all the qRT-PCR assays in this study, the final concentrations of forward primers, reverse primer and hydrolysis probes were 300 nM, 300 nM and 200 nM, respectively. The thermal cycling conditions were 50° C. for 2 minutes, 60° C. for 30 minutes, 95° C. for 5 minutes, followed by 45 cycles of (94° C. for 20 seconds and 60° C. for 1 minute).

The amplification of mRNA target was monitored and analyzed by an ABI Prism 7900 Sequence Detection System (Life Technologies) and Sequence Detection Software version 2.1 (Life Technologies). For each assay, a calibration was prepared by amplifying serial dilutions of HPLC-purified synthetic DNA oligonucleotides (Sigma-Proligo) representing the targeted amplicon at known concentrations. Absolute concentrations of mRNA targets were calculated as the number of copies per ng of total RNA in blood cells. For each blood RNA sample, a normalized marker RNA concentration was calculated by dividing the absolute concentration of the marker RNA (i.e., the B3GNT5 mRNA, the CLC mRNA, and the GBP3 mRNA) by the absolute concentration of the reference RNA (i.e., the GAPDH mRNA). There was no unit to this normalized marker RNA concentration.

QRT-PCR Analysis of RNA Transcripts not Listed in Table 2.

To compare and contrast the predictive performance of the marker RNA transcripts identified in this study (Table 2), two RNA transcripts not listed in Table 2 were analyzed in parallel, namely those coding for the Fc fragment of IgG, low affinity IIIa, receptor (FCGR3A, synonym: CD16A) and the selectin L (SELL, synonym: CD62L). These two RNA transcripts been shown to be highly expressed in blood cells and only lowly expressed in other human cells (Su et al. 2004). Twenty blood RNA samples (10 from the test groups, another 10 from the reference group, Table 3) collected from women were analyzed.

For the CD16A qRT-PCR assay, the forward primer was 5'-ACC CGG TGC AGC TAG AAG TC-3' (SEQ ID NO:10), the reverse primer was 5'-GAA TAG GGT CTT CCT CCT TGA ACA-3' (SEQ ID NO:11), and the hydrolysis probe was 5'(6FAM)-TTG CTC CAG GCC CCT-3'(MGB) (SEQ ID NO:12). For the CD62L qRT-PCR assay, the forward primer was 5'-TTC AGC CTC CCC ACC TTC T-3' (SEQ ID NO:13), the reverse primer was 5'-GGT GTG GAA GTC AGC CAA CTG-3' (SEQ ID NO:14), and the hydrolysis probe was 5'(6FAM)-CAG CCA CCT CTC TT-3'(MGB) (SEQ ID NO:15). Reaction conditions and thermal profile were same as other qRT-PCR assays mentioned above. For each blood RNA sample, normalized concentrations of the CD16A mRNA and the CD62L mRNA were calculated as stated above.

Data from the qRT-PCR Assay Targeting the B3GNT5 mRNA Shortlisted by this Study (Table 2).

Figure 1:
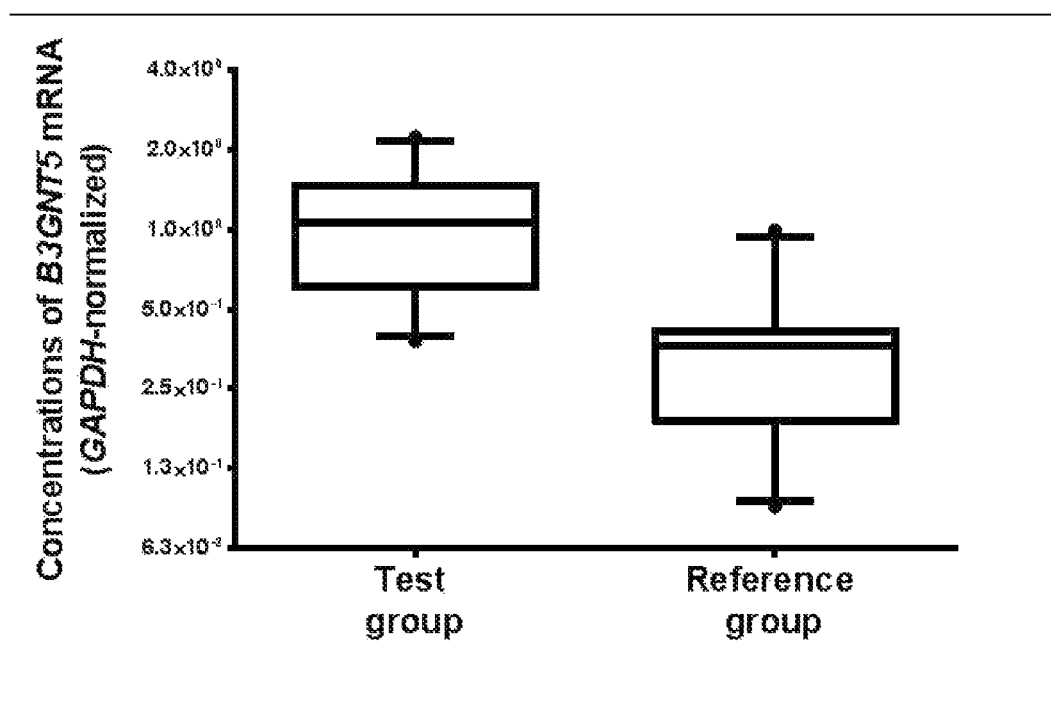
FIG. 1: Box plots of concentrations of the B3GNT5 mRNA in blood of symptomatic women resulting in birth sooner than 34 gestational weeks (test group) and those resulting in birth on or later than 37 weeks (reference group). The box is drawn down to the 25th percentile and up to the 75th percentile. The line inside the box is drawn as the median. The whiskers are drawn down to the 10th percentile and up to the 90th. Points below and above the whiskers are drawn as individual dots.

Blood samples were collected from 20 women during the presentation of regular and frequent uterine contractions. Among them, 10 women resulted in birth sooner than 34 weeks (the test group), and the remaining 10 resulted in birth on or later than 37 weeks (the reference group). The medians (first quartiles-third quartiles) of the GAPDH-normalized blood B3GNT5 mRNA concentrations were 1.06 (0.644-1.44) and 0.362 (0.211-0.391) in the test group and reference group, respectively (FIG. 1). This median normalized B3GNT5 mRNA concentrations in the test group was 2.99-fold higher than that in the reference group (p=0.002, Mann-Whitney rank sum test).

Figure 2:
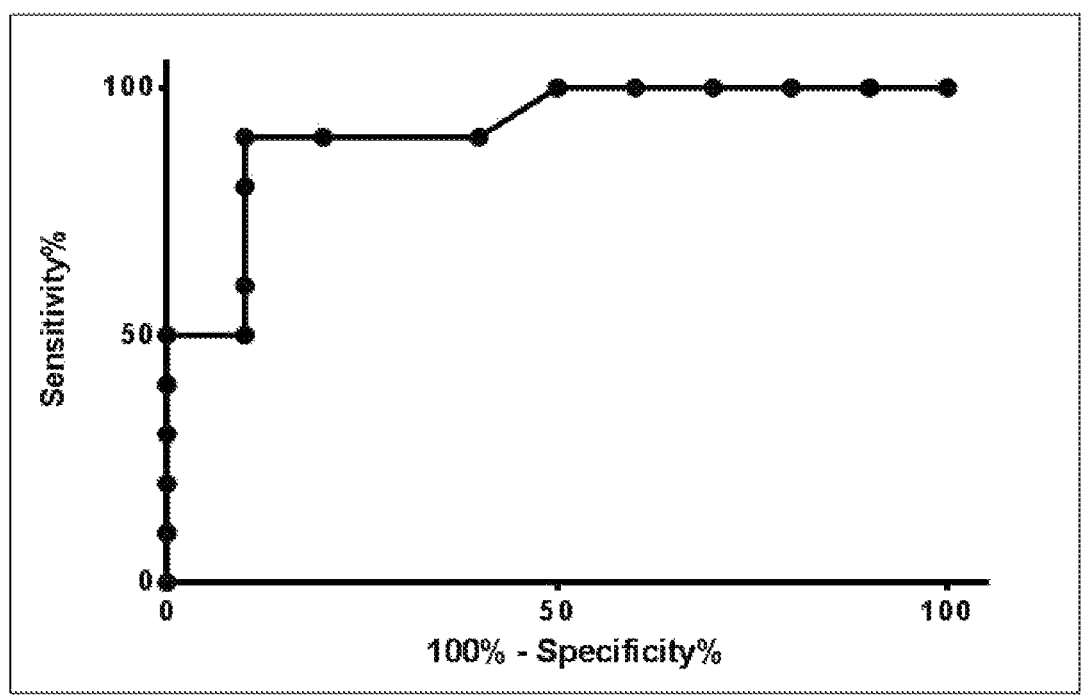
FIG. 2: Receiver-operating characteristics curve of the B3GNT5 mRNA for predicting birth sooner than 34 gestational weeks among symptomatic women.

To determine the optimal threshold concentrations of this marker for identifying birth sooner than 34 weeks, the inventors plotted the receiver-operating characteristics (ROC) curve (FIG. 2, area under curve=0.915, 95% confidence interval (CI)=0.788-1.04, p=0.00172). Using the GAPDH-normalized blood B3GNT5 mRNA concentrations >0.495 as a threshold to define a woman as positive for this assay, the inventors were able to identify the women resulting in birth sooner than 34 weeks at 90.0% sensitivity and 90.0% specificity. The positive predictive value and negative predictive value for the B3GNT5 mRNA are 90.0% and 90.0%, respectively.

Data from the qRT-PCR Assay Targeting the CLC mRNA Shortlisted by this Study (Table 2).

Figure 3:
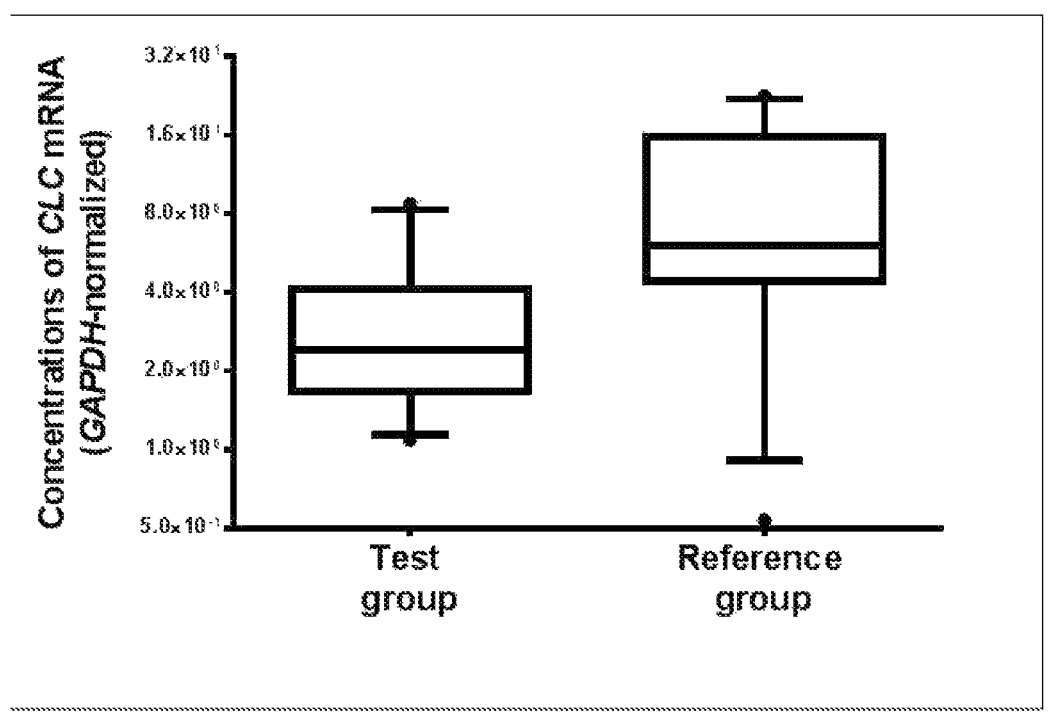
FIG. 3: Box plots of concentrations of CLC mRNA in blood of symptomatic women resulting in birth sooner than 34 gestational weeks (test group) and those resulting in birth on or later than 37 weeks (reference group). The box is drawn down to the 25th percentile and up to the 75th percentile. The line inside the box is drawn as the median.

The medians (first quartiles-third quartiles) of the GAPDH-normalized blood CLC mRNA concentrations were 2.40 (1.68-4.03) and 6.05 (4.43-15.6) in the test group and reference group, respectively (FIG. 3). This median normalized CLC mRNA concentrations in the test group was 2.52-fold lower than that in the reference group (p=0.011, Mann-Whitney rank sum test).

The ROC curve was plotted (FIG. 4, area under curve=0.840, 95% CI=0.637 to 1.04, p=0.0102). Using the GAPDH-normalized blood CLC mRNA concentrations <4.150 as a threshold to define a woman as positive for this assay, the inventors were able to identify the women resulting in birth sooner than 34 weeks at 80% sensitivity and 90% specificity. The positive predictive value and negative predictive value for the CLC mRNA are 88.9% and 81.8%, respectively.

Data from the qRT-PCR Assay Targeting the GBP3 mRNA Shortlisted by this Study (Table 2).

The medians (first quartiles-third quartiles) of the GAPDH-normalized blood GBP3 mRNA concentrations were 0.0587 (0.0134-0.131) and 0.465 (0.107-0.867) in the test group and reference group, respectively (FIG. 5). This median normalized GBP3 mRNA concentrations in the test group was 7.92-fold lower than that in the reference group (p=0.0173, Mann-Whitney rank sum test).

The ROC curve was plotted (FIG. 6, area under curve=0.820, 95% confidence interval=0.624 to 1.02, p=0.0156). Using the GAPDH-normalized blood GBP3 mRNA concentrations <0.0914 as a threshold, the inventors were able to identify the women resulting in birth sooner than 34 weeks at 60% sensitivity and 90% specificity. The positive predictive value and negative predictive value for the GBP3 mRNA are 85.7% and 69.2%, respectively.

Data from the qRT-PCR Assay Targeting the CD16A mRNA not Listed in Table 2.

The medians (first quartiles-third quartiles) of the GAPDH-normalized blood CD16A mRNA concentrations were 365 (267-541) and 341 (300-426) in the test group and reference group, respectively (FIG. 7). This normalized CD16A mRNA concentrations in the test group was not significantly different from those in the reference group (p=0.571, Mann-Whitney rank sum test).

To visualize the predictive performance of the CD16A mRNA, the ROC curve was plotted (FIG. 8). No significant difference was observed between the area of under the ROC curve for CD16A mRNA (area under curve=0.580, 95% CI=0.319 to 0.841) and the area under the identity line (p=0.545). Using the GAPDH-normalized blood CD16A mRNA concentrations >438 as a threshold to define a woman as positive for this test, the inventors were able to identify the women resulting in birth sooner than 34 weeks at 30.0% sensitivity and 90.0% specificity. The positive predictive value and negative predictive value for the CD16A mRNA are 75.0% and 56.3%, respectively.

Data from the qRT-PCR Assay Targeting the CD62L mRNA not Listed in Table 2.

The medians (first quartiles-third quartiles) of the GAPDH-normalized blood CD62L mRNA concentrations were 69.6 (59.7-112) and 76.7 (71.4-91.7) in the test group and reference group, respectively (FIG. 9). This normalized CD62L mRNA concentrations in the test group was not significantly different from those in the reference group (p=0.678, Mann-Whitney rank sum test).

Figure 10:
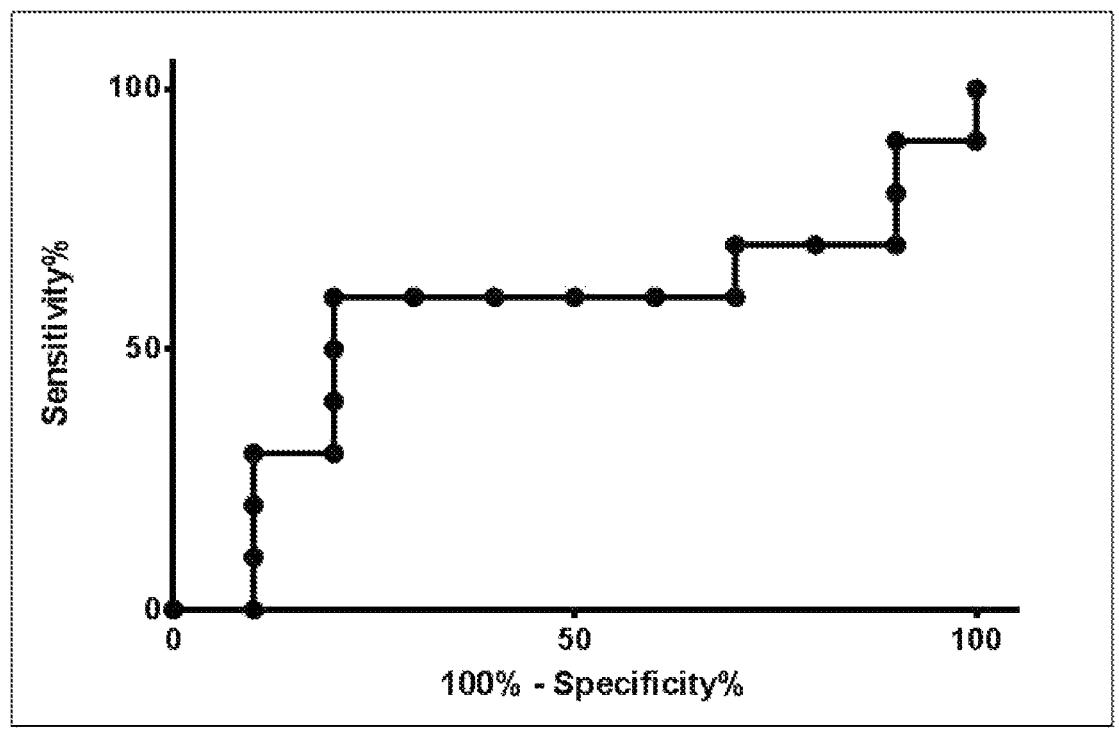

To visualize the predictive performance of the CD62L mRNA, its ROC curve was plotted (FIG. 10). No significant difference was observed between the area of under the ROC curve for CD62L mRNA (0.560, 95% CI=0.288 to 0.832) and the area under the identity line (0.500, p=0.650). Using the GAPDH-normalized blood CD62L mRNA concentrations >62.4 as a threshold to define a woman as positive for this test, the inventors were able to identify the women resulting in birth sooner than 34 weeks at 30.0% sensitivity and 90.0% specificity. The positive predictive value and negative predictive value for the CD16A mRNA are 75.0% and 56.3%, respectively.

Discussions

In this study, using the exon array technology, the present inventors have profiled at the resolution of the exon level the blood transcriptomes of pregnant women during the presentation of uterine contractions. The genome-wide RNA expression data on blood cells during uterine contractions has never been published in the peer-reviewed literature before. Moreover, the inventors have, for the first time, systematically compared the differentially expressed RNA transcripts between the women resulting in birth sooner than 34 gestational week and those resulting in birth on or later than 37 weeks. Furthermore, a method has been devised for the strategic selection of marker RNA transcripts useful predicting birth, among >1.4 million data points of RNA expression levels. These new data and method have enabled investigators in this field to shortlist a panel of 32 RNA transcripts (Table 2), among the >30,000 human genes, which are useful for predicting premature birth via the molecular analysis of maternal peripheral blood.

The inventors have demonstrated the clinical utility of the qRT-PCR assays targeting our shortlisted marker RNA transcripts, namely the B3GNT5 mRNA, the CLC mRNA and the GBP3 mRNA (from Table 2). The concentrations of them were significantly different between women resulting in birth sooner than 34 weeks (the test group) and those resulting in birth on or later than 37 weeks (the reference group; Mann Whitney test, p values=0.002, 0.011 and 0.0173 for the B3GNT5 mRNA, the CLC mRNA and the GBP3 mRNA, respectively). Not only so, the interquartile range of the concentrations two of the three tested markers, B3GNT5 mRNA, the CLC mRNA, had no overlap between the two groups.

In parallel to qRT-PCR assays targeting the marker RNA transcripts shortlisted in this study (from Table 2), the inventors have also analyzed the blood RNA samples of the two groups of participants by assays targeting RNA transcripts not listed in Table 2. In contrast, the GAPDH-normalized concentrations between the two groups were not significantly different (Mann Whitney test, p values=0.571 and 0.678 for the CD16A mRNA and the CD62L mRNA, respectively).

Based on the promising results, the predictive performance of the markers was examined using ROC analyses. For each marker developed in this study (such as those listed in Table 2), the area under the ROC curve was significantly larger than the area under the identity line (x=y), demonstrating a potential use for prediction. Specifically, the areas under curve of the B3GNT5 mRNA, the CLC mRNA and the GBP3 mRNA were 0.915, 0.840, and 0.820, respectively. This indicates that the probabilities of accurately predicting birth sooner than 34 week using the three markers are 91.5%, 84.0% and 82.0%, respectively.

In contrast, the areas under the ROC curves of the CD16A mRNA and the CD62L mRNA were 0.580 and 0.560, respectively. These areas were not significantly different from 0.500, which is the area under the identity line (p=0.545 and 0.650, respectively). This implies that these assays, which were not developed from Table 2, have no potential for predicting birth.

Most importantly, two of the three markers identified by the above strategies have been shown to predict birth at high sensitivity and high specificity. In particular, the sensitivity and specificity for the B3GNT5 mRNA were 90.0% and 90.0%, respectively, and for the CLC mRNA were 88.9% and 81.8%, respectively. The performance of these two novel markers compared favorably to that of transvaginal cervical length (sensitivity and specificity were 63.6% and 85.7%, respectively), or was at least on par with that of fetal fibronectin (sensitivity and specificity were 81.7% and 82.5%, respectively (Lockwood et al. 1991).

Another important advantage of the blood markers shortlisted in this study over transvaginal ultrasonography and fetal fibronectin is that they require no pelvic examination, which is not always tolerable by the pregnant women who need to be tested. To summarize, the present inventors have generated through this study a panel of 32 peripheral blood RNA transcripts, which is useful for prediction of human birth sooner than 34 weeks with better or on par performance compared with current markers.

All patents, patent applications, and other publications, including GenBank Accession Numbers, cited in this application are incorporated by reference in the entirety for all purposes.

LIST OF REFERENCES

Chang C W, Cheng W C, Chen C R, Shu W Y, Tsai M L, Huang C L, Hsu I C. (2011). "Identification of human housekeeping genes and tissue-selective genes by microarray meta-analysis." PLoS One. 6(7):e22859.

Cheng W C, Chang C W, Chen C R, Tsai M L, Shu W Y, Li C Y, Hsu I C. (2011). "Identification of reference genes across physiological states for qRT-PCR through microarray meta-analysis." PLoS One. 6(2):e17347.

Chim S S C, Jin S, Lee T Y H, Lun F M F, Lee W S, Chan L Y S, Jin Y Y, Yang N, Tong Y K, Leung T Y, Lau T K, Ding C, Chiu R W K and Lo Y M D (2008). "Systematic search for placental DNA-methylation markers on chromosome 21: toward a maternal plasma-based epigenetic test for fetal trisomy 21." Clin Chem 54(3): 500-11.

Chim S S C, Lee W S, Ting Y H, Chan O K, Lee S W Y and Leung T Y (2012). "Systematic identification of spontaneous preterm birth-associated RNA transcripts in maternal plasma." PLoS One 7(4): e34328.

Chim S S C, Shing T K F, Hung E C W, Leung T Y, Lau T K, Chiu R W K and Lo Y M D (2008). "Detection and characterization of placental microRNAs in maternal plasma." Clin Chem 54(3): 482-90.

Chim S S C, Tong Y K, Chiu R W K, Lau T K, Leung T N, Chan L Y S, Oudejans C B M, Ding C and Lo Y M D (2005). "Detection of the placental epigenetic signature of the maspin gene in maternal plasma." Proc Natl Acad Sci USA 102(41): 14753-8.

Honest H, Bachmann L M, Coomarasamy A, Gupta J K, Kleijnen J and Khan K S (2003). "Accuracy of cervical transvaginal sonography in predicting preterm birth: a systematic review." Ultrasound Obstet Gynecol 22(3): 305-22.

Honest H, Hyde C J and Khan K S (2012). "Prediction of spontaneous preterm birth: no good test for predicting a spontaneous preterm birth." Curr Opin Obstet Gynecol 24(6): 422-33.

Irizarry R A, Hobbs B, Collin F, Beazer-Barclay Y D, Antonellis K J, Scherf U and Speed T P (2003). "Exploration, normalization, and summaries of high density oligonucleotide array probe level data." Biostatistics 4(2): 249-64.

Lockwood C J, Senyei A E, Dische M R, Casal D, Shah K D, Thung S N, Jones L, Deligdisch L and Garite T J (1991). "Fetal fibronectin in cervical and vaginal secretions as a predictor of preterm delivery." N Engl J Med 325(10): 669-74.

Lui Y Y N, Chik K W, Chiu R W K, Ho C Y, Lam C W K, Lo Y M D. 2002. "Predominant hematopoietic origin of cell-free DNA in plasma and serum after sex-mismatched bone marrow transplantation. Clin Chem. 48(3):421-7.

Murakawa H, Utumi T, Hasegawa I, Tanaka K and Fuzimori R (1993). "Evaluation of threatened preterm delivery by transvaginal ultrasonographic measurement of cervical length." Obstetrics & Gynecology 82(5): 829-832.

Sotiriadis A, Papatheodorou S, Kavvadias A and Makrydimas G (2010). "Transvaginal cervical length measurement for prediction of preterm birth in women with threatened preterm labor: a meta-analysis." Ultrasound Obstet Gynecol 35(1): 54-64.

Storey J D (2002). "A direct approach to false discovery rates." Journal of the Royal Statistical Society: Series B (Statistical Methodology) 64(3): 479-498.

Su A I, Wiltshire T, Batalov S, Lapp H, Ching K A, Block D, Zhang J, Soden R, Hayakawa M, Kreiman G, Cooke M P, Walker J R and Hogenesch J B (2004). "A gene atlas of the mouse and human protein-encoding transcriptomes." Proc Natl Acad Sci USA 101(16): 6062-7.

Tsui D W Y, Lam Y M D, Lee W S, Leung T Y, Lau T K, Lau E T, Tang M H, Akolekar R, Nicolaides K H, Chiu R W K, Lo Y M D and Chim S S C (2010). "Systematic identification of placental epigenetic signatures for the noninvasive prenatal detection of Edwards syndrome." PLoS One 5(11): e15069.

Tsui N B Y, Chim S S C, Chiu R W K, Lau T K, Ng E K O, Leung T N, Tong Y K, Chan K C A and Lo Y M D (2004). "Systematic micro-array based identification of placental mRNA in maternal plasma: towards non-invasive prenatal gene expression profiling." J Med Genet 41(6): 461-7.

TABLE 1

Characteristics of participants in the whole-genome exon array analysis.

| | Resulted in preterm births | Resulted in term births | P-value[a] |
|---|---|---|---|
| Number of participants (n) | 3 | 3 | — |
| Maternal age in years (mean +/− standard deviation (SD)) | 28 +/− 8.5 | 30 +/− 2.6 | 0.7621 |
| Nulliparous (n, %) | 0 (0%) | 1 (33%) | 1.0000 |
| Gestational weeks at blood-taking (mean +/− SD) | 31.5 +/− 0.436 | 31.9 +/− 0.869 | 0.5846 |
| Gestational weeks at delivery (mean +/− SD) | 31.6 +/− 0.515 | 39.3 +/− 0.218 | <=0.0001 |
| Birthweight in grams (mean +/− SD) | 1619 +/− 254.7 | 3095 +/− 172.8 | 0.0011 |
| Maternal white cell count (mean +/− SD) | 9.47 +/− 2.59 | 12.1 +/− 0.808 | 0.1638 |
| Antepartum haemorrhage (n, %) | 1 (33%) | 0 (0%) | 1.00 |

[a]T-test for continuous variables. (Data passed Normality Test and Equal Variance Test.). Fisher Exact test for nominal variables.

TABLE 2

Gene and RNA transcripts identified as useful as blood markers for predicting human birth sooner than 37 weeks.

| Gene Symbol | Gene Name | HGNC ID | RefSeq accession | First quartile of probe signal in test group* | Third quartile of probe signal in test group | First quartile of probe signal in reference group** | Third quartile of probe signal in reference group | Direction of change | Fold-change of median probe signal | q-value |
|---|---|---|---|---|---|---|---|---|---|---|
| B3GNT5 | UDP-GlcNAc: betaGal beta-1,3-N-acetylglucosaminyl-transferase 5 | HGNC: 15684 | NM_032047 | 1533 | 1856 | 627 | 745 | Increased in test group | 2.64 | 0.00740 |
| EFCAB13 | EF-hand calcium binding domain 13 | HGNC: 26864 | NM_152347 | 196 | 206 | 457 | 618 | Decreased in test group | 2.67 | 0.00758 |
| TREML4 | triggering receptor expressed on myeloid cells-like 4 | HGNC: 30607 | NM_198153 | 561 | 624 | 206 | 261 | Increased in test group | 2.78 | 0.00707 |

TABLE 2-continued

Gene and RNA transcripts identified as useful as blood markers for predicting human birth sooner than 37 weeks.

| Gene Symbol | Gene Name | HGNC ID | RefSeq accession | First quartile of probe signal in test group* | Third quartile of probe signal in test group | First quartile of probe signal in reference group** | Third quartile of probe signal in reference group | Direction of change | Fold-change of median probe signal | q-value |
|---|---|---|---|---|---|---|---|---|---|---|
| ADORA3 | adenosine A3 receptor | HGNC: 268 | NM_020683 | 118 | 142 | 349 | 354 | Decreased in test group | 2.88 | 0.00708 |
| PDE6D | phosphodiesterase 6D, cGMP-specific, rod, delta | HGNC: 8788 | NM_002601 | 334 | 388 | 120 | 152 | Increased in test group | 2.88 | 0.00772 |
| CD177 | CD177 molecule | HGNC: 30072 | NM_020406 | 4884 | 5518 | 1387 | 2127 | Increased in test group | 2.90 | 0.00735 |
| SCMH1 | sex comb on midleg homolog 1 (Drosophila) | HGNC: 19003 | NM_001031694 | 89.9 | 105 | 230 | 307 | Decreased in test group | 2.93 | 0.00707 |
| ATP2B4 | ATPase, Ca++ transporting, plasma membrane 4 | HGNC: 817 | NM_001001396 | 782 | 952 | 284 | 342 | Increased in test group | 2.97 | 0.00769 |
| ALDH1A1 | aldehyde dehydrogenase 1 family, member A1 | HGNC: 402 | NM_000689 | 48.8 | 68.1 | 179 | 196 | Decreased in test group | 3.03 | 0.00708 |
| GPR56 | G protein-coupled receptor 56 | HGNC: 4512 | NM_005682 | 606 | 1025 | 223 | 297 | Increased in test group | 3.14 | 0.00708 |
| FAH | fumarylacetoacetate hydrolase (fumarylacetoacetase) | HGNC: 3579 | NM_000137 | 1365 | 1571 | 403 | 541 | Increased in test group | 3.18 | 0.00764 |
| GPR34 | G protein-coupled receptor 34 | HGNC: 4490 | NM_005300 | 154 | 216 | 663 | 852 | Decreased in test group | 3.20 | 0.00708 |
| CLK4 | CDC-like kinase 4 | HGNC: 13659 | NM_020666 | 59.3 | 67.0 | 204 | 211 | Decreased in test group | 3.20 | 0.00684 |
| PTGDR | prostaglandin D2 receptor (DP) | HGNC: 9591 | NM_000953 | 542 | 808 | 208 | 249 | Increased in test group | 3.22 | 0.00724 |
| FNTA | farnesyltransferase, CAAX box, alpha | HGNC: 3782 | NM_002027/ NR_033698/ AB209689 | 77.7 | 109 | 228 | 272 | Decreased in test group | 3.32 | 0.00740 |
| CTSG | cathepsin G | HGNC: 2532 | NM_001911 | 58.2 | 69.0 | 188 | 248 | Decreased in test group | 3.34 | 0.00679 |
| MPO | myeloperoxidase | HGNC: 7218 | NM_000250 | 33.8 | 76.0 | 203 | 272 | Decreased in test group | 3.59 | 0.00758 |
| CPA3 | carboxypeptidase A3 (mast cell) | HGNC: 2298 | NM_001870 | 59.1 | 95 | 272 | 377 | Decreased in test group | 4.23 | 0.00684 |
| LILRA3 | leukocyte immunoglobulin-like receptor, subfamily A (without TM domain), member 3 | HGNC: 6604 | NM_006865 | 212 | 417 | 1145 | 1733 | Decreased in test group | 4.26 | 0.00707 |
| AK5 | adenylate kinase 5 | HGNC: 365 | NM_174858 | 47.2 | 61.1 | 179 | 229 | Decreased in test group | 4.33 | 0.00684 |
| KLRD1 | killer cell lectin-like receptor subfamily D, member 1 | HGNC: 6378 | NM_002262 | 453 | 747 | 140 | 204 | Increased in test group | 4.43 | 0.00735 |
| YPEL1 | yippee-like 1 (Drosophila) | HGNC: 12845 | NM_013313 | 219 | 286 | 51.1 | 70.4 | Increased in test group | 4.58 | 0.00746 |
| NR4A3 | nuclear receptor subfamily 4, group A, member 3 | HGNC: 7982 | NM_006981 | 234 | 450 | 44.7 | 94.3 | Increased in test group | 4.77 | 0.00740 |
| CCR3 | chemokine (C-C motif) receptor 3 | HGNC: 1604 | NM_001837 | 32.6 | 45.7 | 138 | 245 | Decreased in test group | 4.95 | 0.00712 |
| THEM5 | thioesterase superfamily member 5 | HGNC: 26755 | NM_182578 | 297 | 429 | 61.1 | 103 | Increased in test group | 5.01 | 0.00684 |
| KLRC1 | killer cell lectin-like receptor subfamily C, member 1 | HGNC: 6374 | NM_002259 | 153 | 172 | 29.9 | 49.4 | Increased in test group | 5.15 | 0.00746 |

TABLE 2-continued

Gene and RNA transcripts identified as useful as blood markers for predicting human birth sooner than 37 weeks.

| Gene Symbol | Gene Name | HGNC ID | RefSeq accession | First quartile of probe signal in test group* | Third quartile of probe signal in test group | First quartile of probe signal in reference group** | Third quartile of probe signal in reference group | Direction of change | Fold-change of median probe signal | q-value |
|---|---|---|---|---|---|---|---|---|---|---|
| CLC | Charcot-Leyden crystal galectin | HGNC: 2014 | NM_001828 | 790 | 1049 | 3510 | 4871 | Decreased in test group | 5.55 | 0.00737 |
| GBP3 | guanylate binding protein 3 | HGNC: 4184 | NM_018284 | 12.9 | 23.5 | 133 | 266 | Decreased in test group | 7.86 | 0.00764 |
| HSD17B4 | hydroxysteroid (17-beta) dehydrogenase 4 | HGNC: 5213 | NM_000414 | 36.0 | 47.6 | 302 | 339 | Decreased in test group | 8.81 | 0.00684 |
| IL5RA | interleukin 5 receptor, alpha | HGNC: 6017 | NM_000564 | 21.3 | 32.9 | 216 | 310 | Decreased in test group | 9.64 | 0.00740 |
| HRH4 | histamine receptor H4 | HGNC: 17383 | NM_021624 | 14.9 | 19.7 | 127 | 191 | Decreased in test group | 9.71 | 0.00740 |
| EDIL3 | EGF-like repeats and discoidin I-like domains 3 | HGNC: 3173 | NM_005711 | 10.8 | 12.4 | 208 | 363 | Decreased in test group | 29.0 | 0.00708 |

Legend:
HGNC: HUGO Gene Nomenclature Committee at the European Bioinformatics Institute (http://www.genenames.org/).
RefSeq: Reference Sequence Database at the National Center for Biotechnology Information, National Library of Medicine (http://http://www.ncbi.nlm.nih.gov/refseq/)
q-value: False Discovery Rate adjusted p-values
*Test group comprised women with uterine contractions (<34 gestational weeks) and resulting in birth sooner than 34 weeks.
**Reference group comprised women with uterine contractions (<34 weeks) and resulting in birth on or later than 37 weeks.

TABLE 3

Characteristics of participants for qRT-PCR analysis.

| | Resulted in preterm births | Resulted in term births | P-value[a] |
|---|---|---|---|
| Number of participants with uterine contractions at blood-taking (n) | 10 | 10 | — |
| Maternal age in years (mean +/− standard deviation (SD)) | 30 +/− 7.4 | 33 +/− 5.8 | 0.3088 |
| Nulliparous (n, %) | 4 (40%) | 4 (40%) | 1.00 |
| Gestational weeks at blood-taking (mean +/− SD) | 31.7 +/− 2.34 | 29.8 +/− 2.59 | 0.0976 |
| Gestational weeks at delivery (mean +/− SD) | 31.9 +/− 2.13 | 39.4 +/− 1.06 | <0.0001 |
| Birthweight in grams (mean +/− SD) | 1735 +/− 470.2 | 3519 +/− 432.6 | <0.0001 |
| Maternal white cell count in $10^9$ per L (mean +/− SD) | 13.4 +/− 4.33 | 10.4 +/− 1.75 | 0.0565 |
| Antepartum haemorrhage (n, %) | 3 (30%) | 1 (10%) | 0.582 |
| Prelabor rupture of membrane (n, %) | 7 (70%) | 4 (40%) | 0.370 |

[a]T-test for continuous variables. (Data passed Normality Test and Equal Variance Test.). Fisher Exact test for nominal variables.

What is claimed is:

1. A method for prophylactic treatment of premature birth, comprising the steps of:
   (a) measuring mRNA level of marker gene ATP2B4 in a blood sample taken from a pregnant woman; and
   (b) detecting the ATP2B4 mRNA level obtained in step (a) to be higher than a standard control, and determining the woman as having increased risk of premature birth; and
   (c) providing prophylactic treatment for premature birth to the woman determined in step (b) as having increased risk of premature birth, wherein the prophylactic treatment comprises administration of an antenatal corticosteroid, a tocolytic drug, or transdermal glyceryl trinitrate.

2. The method of claim 1, wherein the sample is whole blood.

3. The method of claim 1, wherein the sample is isolated blood cells.

4. The method of claim 1, wherein the sample is plasma.

5. The method of claim 1, wherein the sample is serum.

6. The method of claim 1, wherein the mRNA level is normalized over the mRNA level of a reference gene in the same sample prior to step (b).

7. The method of claim 1, wherein step (a) comprises mass spectrometry or hybridization to a microarray, fluorescence probe, or molecular beacon.

8. The method of claim 1, wherein step (a) comprises an amplification reaction.

9. The method of claim 8, wherein the amplification reaction is a polymerase chain reaction (PCR).

10. The method of claim 9, wherein the PCR is a reverse transcriptase-PCR (RT-PCR).

11. The method of claim 1, wherein step (a) comprises a polynucleotide hybridization assay utilizing a polynucleotide probe comprising a detectable moiety.

12. The method of claim 11, wherein the polynucleotide hybridization assay is a Southern Blot analysis, Northern Blot analysis, or an in situ hybridization assay.

13. The method of claim 1, wherein the mRNA level is normalized over the mRNA level of a reference gene in the same sample prior to step (b).

14. The method of claim 13, wherein the reference gene is GAPDH.

15. The method of claim 1, when the woman is indicated as having increased risk of premature birth, further comprising a step of treating the woman for premature birth.

16. The method of claim 1, wherein the mRNA level of more than one marker genes is measured and compared with their respective standard controls to determine risk of premature birth.

* * * * *